(12) United States Patent
Govari et al.

(10) Patent No.: US 10,980,983 B2
(45) Date of Patent: Apr. 20, 2021

(54) EAR-NOSE-THROAT (ENT) HOLLOW GUIDE WIRE WITH BALLOON

(71) Applicant: Biosense Webster (Israel) Ltd., Yokneam (IL)

(72) Inventors: Assaf Govari, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 108 days.

(21) Appl. No.: 16/234,601

(22) Filed: Dec. 28, 2018

(65) Prior Publication Data

US 2020/0206473 A1    Jul. 2, 2020

(51) Int. Cl.
*A61M 25/09*    (2006.01)
*A61M 25/01*    (2006.01)
*A61M 29/02*    (2006.01)

(52) U.S. Cl.
CPC ........ *A61M 25/09* (2013.01); *A61M 25/0127* (2013.01); *A61M 29/02* (2013.01);
(Continued)

(58) Field of Classification Search
CPC ........... A61B 17/24; A61B 1/233; A61B 1/07; A61B 1/227; A61B 2034/2051; A61B 5/062; A61B 17/12104; A61B 1/00096; A61B 2017/00787; A61B 2017/22051; A61B 34/20; A61B 5/036; A61B 5/415; A61B 5/6851; A61B 8/12; A61B 17/00234; A61B 17/1204; A61B 17/12131; A61B 17/12136; A61B 17/1771; A61B 17/1785; A61B 2017/00557; A61B 2017/22038; A61B 2018/00327; A61B 2034/2072; A61B 5/6853; A61B 90/361; A61M 25/09; A61M 25/0127; A61M 29/02; A61M 2025/0166; A61M 2025/09066;
(Continued)

(56) References Cited

U.S. PATENT DOCUMENTS 4,946,466 A * 8/1990 Pinchuk ................ A61M 25/09
 604/913
5,167,239 A * 12/1992 Cohen .............. A61B 17/22032
 600/434
(Continued)

FOREIGN PATENT DOCUMENTS

EP    0376132    7/1990
EP    3173045    5/2017
(Continued)

OTHER PUBLICATIONS

European Search Report dated Jun. 18, 2020 from corresponding European Patent Application No. 19219594.9.

*Primary Examiner* — Katherine M Shi
(74) *Attorney, Agent, or Firm* — Todd J. Burns

(57) ABSTRACT

A medical probe includes a hollow guidewire, a balloon, and a magnetic position sensor. The hollow guidewire is configured for insertion into a channel of an organ of a patient. The balloon is fixed to a distal end of the hollow guidewire, is configured to be inserted into the channel using the hollow guidewire, and is further configured to be inflated by pumping of fluid through the hollow guidewire. The magnetic position sensor is fitted at the distal end of the hollow guidewire.

4 Claims, 3 Drawing Sheets

(52) U.S. Cl.
CPC ........... *A61M 2025/0166* (2013.01); *A61M 2025/09066* (2013.01); *A61M 2025/09108* (2013.01); *A61M 2210/0618* (2013.01); *A61M 2210/0675* (2013.01)

(58) Field of Classification Search
CPC .......... A61M 2025/09108; A61M 2210/0618; A61M 2210/0675; A61M 25/005; A61M 2025/09008; A61M 2025/09175; A61M 25/10; A61M 2210/0681; A61F 11/004; A61F 11/00
See application file for complete search history.

(56) References Cited

U.S. PATENT DOCUMENTS

| | | | |
|---|---|---|---|
| 6,491,712 B1* | 12/2002 | O'Connor | A61B 17/12109 606/200 |
| 2002/0169472 A1 | 11/2002 | Nareak et al. | |
| 2009/0292225 A1* | 11/2009 | Chen | A61M 25/09033 600/585 |
| 2010/0069950 A1* | 3/2010 | Rabbitte | A61M 25/104 606/200 |
| 2010/0113918 A1* | 5/2010 | Anderson | A61B 5/061 600/424 |
| 2010/0198191 A1 | 8/2010 | Clifford et al. | |
| 2013/0274715 A1 | 10/2013 | Chan et al. | |
| 2015/0202089 A1 | 7/2015 | Campbell et al. | |
| 2017/0135754 A1* | 5/2017 | Gliner | A61B 18/1485 |
| 2018/0036009 A1 | 2/2018 | Zoabi et al. | |

FOREIGN PATENT DOCUMENTS

| | | |
|---|---|---|
| EP | 3315163 | 5/2018 |
| WO | WO 1992/021282 | 12/1992 |
| WO | WO 2018/042271 | 3/2018 |

* cited by examiner

EAR-NOSE-THROAT (ENT) HOLLOW GUIDE WIRE WITH BALLOON

FIELD OF THE INVENTION

The present invention relates generally to medical probes, and particularly to ear-nose-throat (ENT) catheters.

BACKGROUND OF THE INVENTION

Various probes have been proposed for ear, nose, and throat (ENT) therapeutic procedures. For example, U.S. Patent Application Publication 2010/0198191 describes methods and systems for accessing a Eustachian tube of a patient. The system includes a guide configured for passing into a nasal passage of the patient to position a distal tip of the catheter at or near a Eustachian tube, the guide having a distal tip with a bend having an angle between 30 and 90 degrees; and a guidewire configured to pass through the guide into the Eustachian tube. A device for providing therapy to the Eustachian tube is passed through the guide. In an embodiment, a dilating balloon is being introduced over a guidewire.

As another example, U.S. Patent Application Publication 2015/0202089 describes an apparatus comprises a shaft, an expandable dilator, and at least one ventilation pathway. The shaft defines a longitudinal axis and comprises distal and proximal ends with at least one shaft lumen. The expandable dilator comprises body with its own proximal and distal ends. The body is configured to transition between a contracted state and an expanded state. The body is configured to dilate a Eustachian tube of a patient in the expanded state. In some embodiments, one or more feature, dimension or the like of such catheters may be altered to facilitate use of the balloon catheter in a Eustachian tube.

U.S. Patent Application Publication 2013/0274715 describes a device and method for dilating a Eustachian tube of a patient. The device includes a guide catheter and a balloon dilation catheter. The balloon dilation catheter has an actuator that prevents injury to the middle ear. The balloon dilation catheter is slidably coupled with the guide catheter through the guide catheter lumen and is fully inserted into the guide catheter lumen when the distal side of the actuator is adjacent to the proximal end of the guide catheter. The method involves advancing the guide catheter and balloon dilation catheter through a nasal passage of the patient to dilate a portion of the Eustachian tube.

U.S. Patent Application Publication 2018/0036009 describes a method that includes inserting into a patient organ a catheter including a position sensor, a device and a handle. The position sensor is attached to a distal end of the catheter. The device is movable along the catheter. The handle includes a control for navigating the device along the catheter to a target location in the patient organ. Based on a location of the position sensor, a target position of the control on the handle that corresponds to the target location of the device is estimated. A marker is set to mark the target position of the control on the handle, and the device is navigated to the target location by setting the control to the marker. In an embodiment, the handle comprises a balloon slider, which is configured to move a balloon along a guidewire, so as to position the balloon at a location of treatment.

SUMMARY OF THE INVENTION

An embodiment of the present invention provides a medical probe including a hollow guidewire, a balloon, and a magnetic position sensor. The hollow guidewire is configured for insertion into a channel of an organ of a patient. The balloon is fixed to a distal end of the hollow guidewire, is configured to be inserted into the channel using the hollow guidewire, and is further configured to be inflated by pumping of fluid through the hollow guidewire. The magnetic position sensor is fitted at the distal end of the hollow guidewire.

In some embodiments, the hollow guidewire includes a coil-reinforced polyimide polymer tube. In some embodiments, the hollow guidewire includes a braid-reinforced polymer tube. In an embodiment, a distal edge of the hollow guidewire protrudes beyond the balloon.

In another embodiment, the magnetic position sensor is formed on a flexible printed-circuit-board wrapped around the distal end of the hollow guidewire.

There is additionally provided, in accordance with an embodiment of the present invention, a manufacturing method, including providing a hollow guidewire for insertion into a channel of an organ of a patient. A balloon is attached to a distal end of the hollow guidewire so that the hollow guidewire protrudes beyond the balloon. A magnetic position sensor is fitted at the distal end of the hollow guidewire.

In some embodiments, providing the hollow guidewire includes providing a coil-reinforced polymer tube. In some embodiments, providing the hollow guidewire includes providing a braid-reinforced polymer tube.

In an embodiment, the distal edge of the hollow guidewire protrudes beyond the balloon and both ends of the balloon are secured to the distal end of the hollow guidewire. In another embodiment, the method includes securing both ends of the balloon to the hollow guidewire by gluing both ends of the balloon to the hollow guidewire. In some embodiments, the method includes securing both ends of the balloon to the hollow guidewire by melting both ends of the balloon to the hollow guidewire.

In an embodiment, fitting the magnetic position sensor includes forming the magnetic position sensor on a flexible printed-circuit-board wrapped around the distal end of the hollow guidewire.

There is further provided, in accordance with an embodiment of the present invention, a method, including inserting a balloon attached to a hollow guidewire into a channel of an organ of a patient, wherein the balloon is configured to be inflated or deflated through one or more side holes in the hollow guidewire. The balloon is navigated in the channel using a magnetic sensor fitted at the distal end of the hollow guidewire. The balloon is inflated by pumping fluid through the hollow guidewire to dilate the channel.

In some embodiments, the method further includes deflating the balloon through the hollow guidewire, and retracting the balloon by pulling the hollow guidewire out of the organ of the patient.

The present invention will be more fully understood from the following detailed description of the embodiments thereof, taken together with the drawings in which:

DETAILED DESCRIPTION OF EMBODIMENTS

Overview

Figure 1:
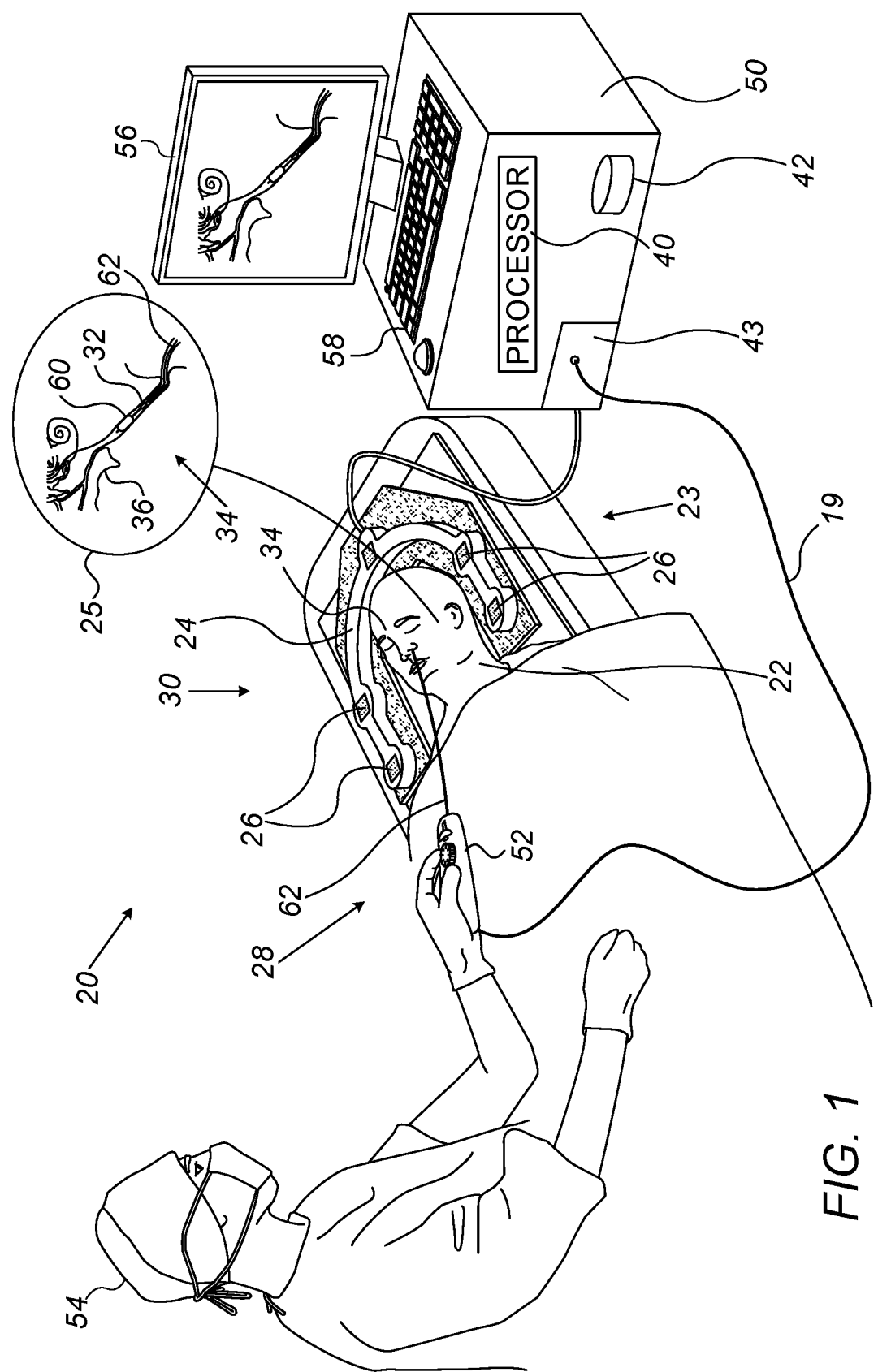
FIG. 1 is a schematic, pictorial illustration of an ear, nose, and throat (ENT) catheterization system, in accordance with an embodiment of the present invention.

An unusually narrow channel in a patient's head may cause, or worsen, an ear, nose, and throat (ENT) medical condition. For instance, a eustachian tube may be exceptionally narrow, and/or may be blocked by wax, which may cause repeated ear infections. As another example, the tear ducts also include very narrow channels that may benefit from being enlarged. These, and other related ENT medical conditions, may be relieved by dilating the blocked channel. However, there is no easy way to enlarge such channels at present.

Embodiments of the present invention that are described hereinafter provide an ENT probe that has an exceptionally small diameter, on the order of several hundred microns. The disclosed ENT probe is intended to be used in narrow channels such as the tear ducts, channels in the brain, channels in the sinuses and the eustachian tube.

Typically, the distal end of the probe is advanced through a small diameter sheath (e.g., in a range of 300-500 microns) to provide the probe passage with sufficient maneuverability in the narrow channel. The probe is made of a hollow guidewire with a miniature "plasty" balloon directly attached to the distal end of the guidewire, enabling balloon inflation up to a diameter of few millimeters. In the present context, the term "plasty balloon" (as opposed to an elastic balloon) means that once inflated, the balloon remains in its dilated form and approximate size even when internal pressure is increased.

The disclosed guidewire is hollow in order to inject (e.g., pump) and/or withdraw fluid used to inflate and/or deflate the balloon. In some embodiments, holes are made in the walls of the balloon where the balloon is fitted over the distal end of the hollow guidewire. The distal edge of the hollow guidewire protrudes beyond the balloon, and the distal end of the hollow guidewire is fixed (e.g., glued) to the balloon at a proximal end and distal end of the balloon over a perimeter of the hollow guidewire. The balloon is pumped through one or more side holes in the hollow guidewire, so as to contain the high fluid pressures inside the balloon, as is typically necessary in plastic dilation procedures.

In some embodiments, the hollow guidewire wall is made of a coil-reinforced thin-wall polyimide polymer tube. The metal wire in the polyimide wall, or other suitable plastic, serves to limit expansion of the tube due to high internal pressures while not limiting maneuverability. Such a reinforced tube can withstand the high pressure of fluid being streamed inside the tube during a dilation procedure. Alternatively, the tube may be reinforced with a braid rather than a coil.

In some embodiments, the disclosed ENT probe includes a magnetic position sensor at its distal end, which is used for tracking the location of the distal end in the head during the ENT procedure. The magnetic position sensor may contain a single-, double-, or triple-axis magnetic transducer, and may assist, for example, in positioning the balloon at a target location for dilation in the channel.

In some embodiments, in order to conform with the small diameter sheath, the magnetic position sensor is formed on a flexible printed circuit board (PCB) wrapped around the ultra-thin hollow guidewire. A similar magnetic position sensor, which is formed on a flexible PCB wrapped around a distal end of a sheath of a catheter, is described in U.S. Provisional Patent Application 62/675,952, filed May 24, 2018, entitled "Position Sensor on Brain Clot Sheath and Location Pad Collar," which is assigned to the assignee of the present patent application and whose disclosure is incorporated herein by reference.

The disclosed hollow guidewire attached to a dilation balloon which is dilated by streaming high-pressure fluid via the ultra-thin guidewire, may enable minimally invasive ENT treatments that larger diameter probes cannot perform.

System Description

FIG. 1 is a schematic, pictorial illustration of an ear, nose, and throat (ENT) catheterization system 20, in accordance with an embodiment of the present invention. System 20 comprises a probe that is configured and used, by way of example, to dilate a eustachian tube of a patient at a given location over the eustachian tube, as described below.

A processor 40 of system 20 registers, with a coordinate system of system 20, frames of reference of a CT (computerized tomography) image of patient 22 comprising an image of the eustachian tube. Data of the CT image is stored in memory 42 for subsequent retrieval by processor 40.

During the exemplified balloon dilation procedure, and as shown in inset 25, a magnetic tracking sub-system 23 of system 20 tracks a position of magnetic position sensor 32 inside eustachian tube 36 of patient 22. In parallel, processor 40 registers the magnetically tracked position with the CT images. As further shown in inset 25, magnetic position sensor 32 is fitted at the distal end of the hollow guidewire by wrapping sensor 32 around a hollow guidewire 62 at a distal end 34 of ENT probe 28, just proximally to a dilation balloon 60.

Magnetic tracking sub-system 23 comprises a magnetic radiator assembly 24, which is positioned beneath the patient's head. Assembly 24 comprises magnetic field radiators 26 which are fixed in position and which transmit alternating sinusoidal magnetic fields into a region 30 within which the head of patient 22 is located. By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention. The Carto®3 catheter-based magnetic tracking system, produced by Biosense Webster, Irvine, Calif., is similar to sub-system 23.

Elements of system 20 are controlled by a system processor 40, comprising a processing unit communicating with one or more memories. Processor 40 may be mounted in a console 50, which comprises operating controls 58 that typically include a keypad and/or a pointing device such as a mouse or trackball. Console 50 connects to the radiators via a cable and/or wirelessly, and also connects to other elements of system 20, such as controller 52 of probe 28.

For the registration performed by system 20, just prior to its insertion into eustachian tube 36, distal end 34 of ENT probe 28 is touched to different regions of the skin of patient 22. The signals induced in the sensor in response to its interaction with the magnetic fields enable the position of distal end 34 to be tracked once assembly 24 has been calibrated. A probe controller 52, held by a physician 54 operating system 20, is connected to the proximal end of ENT probe 28, the controller allowing the physician to control acquisition of the signals from sensor 32.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm that enables processor 40 to perform the disclosed position tracking and registration steps.

ENT Hollow Guidewire with Attached Balloon

Figure 2:
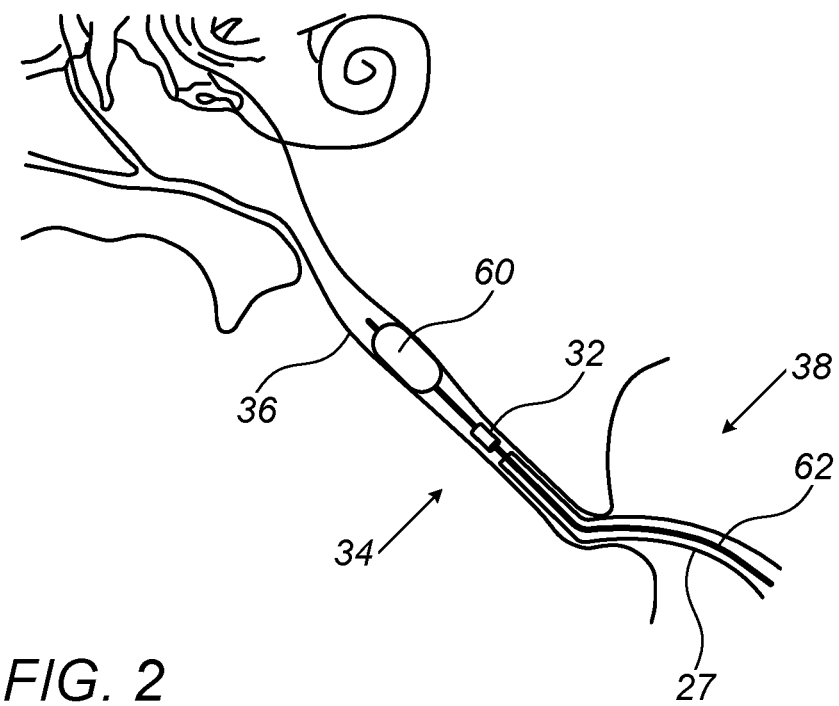
FIG. 2 is a side-view of the distal end of the ENT probe of FIG. 1 inside a eustachian tube, in accordance with an embodiment of the present invention.

FIG. 2 is a side-view of distal end 34 of the ENT probe 28 of FIG. 1 inside eustachian tube 36, in accordance with an embodiment of the present invention. Distal end 34 is seen after being advanced through a small diameter sheath 27 through which hollow guidewire 62 is inserted to eustachian tube 36 from the nasal cavity through an anatomical opening 38. Hollow guidewire 62 has an exceptionally low diameter, on the order of several hundred microns, while still being stiff enough, as described below, to be inserted into a channel blocked by media such as dense mucus.

Balloon 60, which is attached to the distal edge of hollow guidewire 62, is navigated to and placed at a target location inside eustachian tube 36 using magnetic position tracing sub-system 23 that tracks the location of magnetic position sensor 32. FIG. 2 further shows balloon 60 inflated through hollow guidewire 62, dilating eustachian tube 36.

The example illustration shown in FIG. 2 is chosen purely for the sake of conceptual clarity. FIG. 2 shows only parts relevant to embodiments of the present invention. Other system elements, such as means for optical imaging, or drug delivery, are omitted for clarity.

Figure 3:
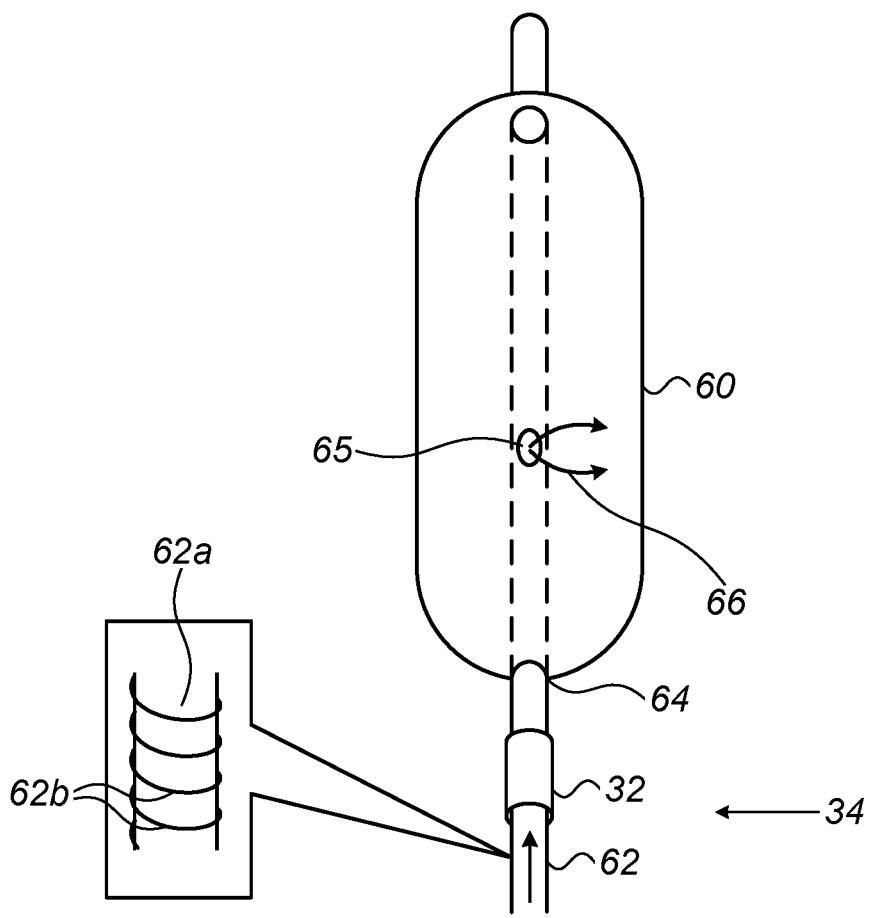
FIG. 3 is a schematic, pictorial illustration of the distal end of the ENT probe of FIG. 2, in accordance with an embodiment of the present invention.

FIG. 3 is a schematic, pictorial illustration of distal end 34 of ENT probe 28 of FIG. 2, in accordance with an embodiment of the present invention. In the shown embodiment, balloon 60 is glued to hollow guidewire 62 at a proximal perimeter 64 of a hole made in balloon 60 through which hollow guidewire 62 was inserted into balloon 60. Guidewire 62, which is sealed at its distal edge, is going through the balloon with the distal edge exiting balloon 60. The balloon is glued to the distal end of guidewire 62 over a distal perimeter (not shown). By guidewire 62 protruding beyond balloon 60, physician 54 is able to advance the still collapsed balloon (not seen) through a narrow channel.

Hollow guidewire 62 enables fluid to flow into the balloon through a side hole 65, as illustrated by arrows 66. Fluid, for example, saline solution may be pumped into balloon 60, so as to inflate balloon to high pressure and then once desired, fluid may be pumped out of balloon to deflate the balloon.

In some embodiments, the wall of hollow guidewire 62 is made of a thin-wall polyimide tube 62a reinforced with a metal coil 62b. In an embodiment, polyimide wall 62a, or another suitable plastic, has the metal wire of coil 62b braided in which serves to limit expansion of the tube due to high internal pressures while not limiting maneuverability. Such a reinforced tube can withstand high-pressure fluid streaming inside the tube during a dilation procedure, and provide the required stiffness to overcome mechanical resistance for insertion of probe 28 into a channel, resulting, for example, from blocking mucus.

Balloon 60 is configured to remain in its dilated form and main a same approximate size (e.g., up to ±10%) over a wide range of internal pressure between a few atmospheres and fifteen atmospheres. This way, balloon 60 can be used for dilating narrow channels to a predetermined diameter in a controlled and safe manner.

In some embodiments, the disclosed ENT probe includes magnetic position sensor 32, which is used for tracking a location of balloon 60 (e.g. inside eustachian tube 36) during the ENT procedure. The disclosed magnetic position sensor may contain a single-, double-, or triple-axis magnetic transducer. In order to conform with the small diameter required of distal end 34, magnetic position sensor 32 is formed on a flexible printed circuit board wrapped around the ultra-thin hollow guidewire, as noted above.

The example illustration shown in FIG. 3 is chosen purely for the sake of conceptual clarity. FIG. 3 shows only parts relevant to embodiments of the present invention. Additional elements, such as electrical wires, possible temperature sensors, and irrigation holes for infusion of a drug, are omitted for clarity of presentation.

Figure 4:
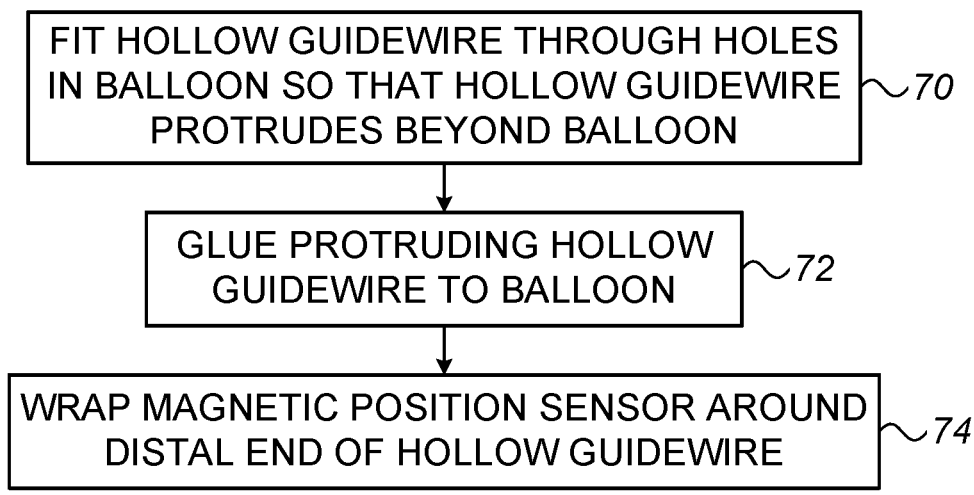
FIG. 4 is a flow chart that schematically illustrates a manufacturing method of the ENT probe of FIG. 3, in accordance with an embodiment of the present invention.

FIG. 4 is a flow chart that schematically illustrates a manufacturing method of the ENT probe of FIG. 3, in accordance with an embodiment of the present invention. The process begins with fitting a reinforced hollow guidewire 62 having a side hole 65 and an occluded distal end through proximal and distal holes in balloon 60 so that hollow guidewire 62 protrudes beyond the balloon, in a balloon fitting manufacturing step 70. Next, the protruding hollow guidewire is glued to balloon 60 over a proximal perimeter 64 and over a distal perimeter (not shown), at a balloon gluing manufacturing step 72. Alternatively, heat may be used to melt proximal and or distal perimeters of balloon to exterior guidewire surface. At a magnetic position sensor disposing step 74, magnetic position sensor 32 is wrapped around the distal end of hollow guide wire 62, and glued together with its electrical leads (not shown).

The example flow chart shown in FIG. 4 is chosen purely for the sake of conceptual clarity. Additional steps, such as connecting electrical wires to sensor 32 are omitted to simplify presentation. A more detailed description of steps of manufacturing is omitted for simplicity.

Figure 5:
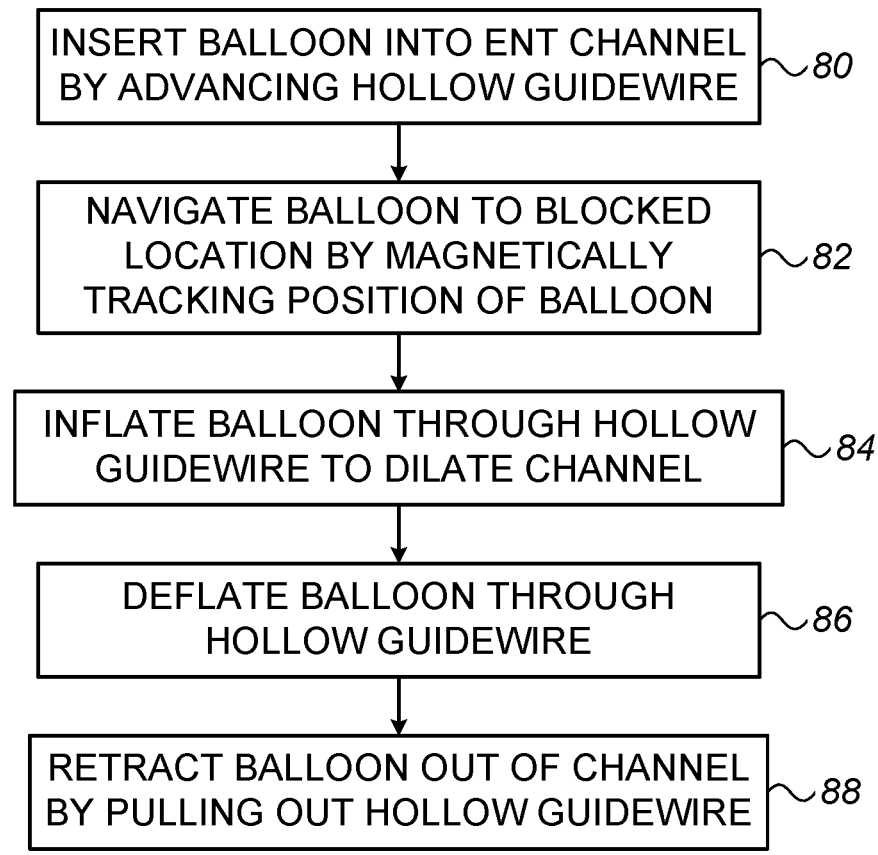
FIG. 5 is a flow chart that schematically illustrates a method for dilating an ENT channel, in accordance with an embodiment of the present invention.

FIG. 5 is a flow chart that schematically illustrates a method for dilating an ENT channel, in accordance with an embodiment of the present invention. The medical procedure begins with physician 54 inserting balloon 60 into an ENT channel, such as eustachian tube 36, by advancing hollow guidewire 62, at a balloon insertion step 80. Next, physician 54 uses system 20 to navigate and position balloon 60 at a blocked location inside the channel, at a balloon positioning step 82. Physician 54 then dilates the channel by inflating balloon 60, by flowing high pressure saline solution into the balloon through hollow guidewire 62, at a balloon dilation step 84. After physician 54 decides that the dilation suffices, the physician deflates balloon 60, at a balloon deflation step 86. Finally, physician 54 retracts balloon 60 from the ENT channel by pulling out hollow guidewire 62, at a balloon retraction step 88.

Although the embodiments described herein mainly address ENT applications, the methods and systems described herein can also be used in other applications, such as in minimally invasive procedures in neurology or cardiology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A medical probe, comprising:
   a hollow guidewire for insertion into a channel of an organ of a patient;
   a balloon fixed to a distal end of the hollow guidewire, wherein the balloon is configured to be inserted into the channel using the hollow guidewire and is further configured to be inflated by pumping of fluid through the hollow guidewire; and
   a magnetic position sensor fitted at the distal end of the hollow guidewire, wherein the magnetic position sensor is formed on a flexible printed-circuit-board wrapped around an exterior of the distal end of the hollow guidewire.

2. The medical probe according to claim 1, wherein the hollow guidewire comprises a coil-reinforced polyimide polymer tube.

3. The medical probe according to claim 1, wherein the hollow guidewire comprises a braid-reinforced polymer tube.

4. The medical probe according to claim 1, wherein a distal edge of the hollow guidewire protrudes beyond the balloon.

* * * * *